United States Patent [19]

Stief et al.

[11] Patent Number: 6,083,483
[45] Date of Patent: Jul. 4, 2000

[54] INHIBITORS OF PHOSPHODIESTERASE IV FOR X-RAY IMAGING

[75] Inventors: Christian Stief, Hemmingen; Torsten Strohmeyer, Berlin; Wolf-Georg Forssmann, Blucherstr. 5, D-30175 Hannover; Markus Meyer, Hannover; Peter Schulz-Knappe, Hannover, all of Germany; Akmal Taher, Jakarta, Indonesia

[73] Assignee: Wolf-Georg Forssmann, Germany

[21] Appl. No.: 09/272,759

[22] Filed: Mar. 19, 1999

Related U.S. Application Data

[62] Division of application No. 08/937,590, Sep. 29, 1997, Pat. No. 5,891,904, which is a continuation of application No. 08/403,823, filed as application No. PCT/DE93/00892, Sep. 14, 1993, abandoned.

[30] Foreign Application Priority Data

Sep. 14, 1992 [DE] Germany ............................. 42 30 755
Jul. 17, 1993 [DE] Germany ............................. 43 24 571

[51] Int. Cl.⁷ ............................. A61K 49/04; A61B 5/055
[52] U.S. Cl. ............................. 424/9.4; 424/9.3; 424/9.5
[58] Field of Search ............................. 424/9.4, 9.41, 424/9.411, 9.42, 9.43, 9.44, 9.45, 9.3, 9.5

[56] References Cited

PUBLICATIONS

Truss et al., Urol Res (1996) Springer–Verlag pp. 129–134.
Taher et al., World J Urol 1997 Springer–Verlag 1997, vol. 15, pp. 32–35.
Hermann Tenor and Christian Schudt. Phosphodiesterase Inhibitors (1996) pp. 21–23; and 34.
Stief et al., Urol Int. (1995) vol. 55, pp 183–189.
Goodman and Gilman, *The Pharm. Basis of Ther.,* (1975) 5th ed., p. 735.
Giembycz et al., *Biochemical Pharmacology,* (1991) vol. 42, No. 3, pp 663–677.
Nicholson et al., *Trends in Pharmacological Sciences,* (1991) vol. 12, No. 1, pp. 19–27.
Dorland's Illustrated Medical Dictionary, (1965) 24th ed., p. 952.
Takashi Morita et al., *Tohoku J. Exp. Med.,* (1987) vol. 151, pp. 201–204.
R. M. Weiss et al., *J. of Pharm. and Exp. Ther.,* (1988) vol. 247, No. 2, pp. 630–634.

*Primary Examiner*—José G. Dees
*Assistant Examiner*—Michael G. Hartley
*Attorney, Agent, or Firm*—Millen, White, Zelano, & Branigan, P.C.

[57] ABSTRACT

The invention relates to the use of inhibitors of phosphodiesterase IV for the modulation of the motility and peristalsis of the hollow organs of the urogenital and gastrointestinal tract.

12 Claims, 3 Drawing Sheets

INHIBITORS OF PHOSPHODIESTERASE IV FOR X-RAY IMAGING

This is a divisional application of Ser. No. 08/937,590 filed Sep. 29, 1997 now U.S. Pat. No. 5,891,904; which is a continuation of Ser. No. 08/403,823, filed Jun. 1, 1995, now abandoned, which is a 371 of PCT/DE93/00892, filed Sep. 14, 1993.

The invention relates to the use of inhibitors of phosphodiesterase IV (sPDE IV) for the production of pharmaceutical agents for the modulation of the motility and peristalsis of the hollow organs of the urogenital and gastrointestinal tract as well as their use as adjuvants for contrast medium studies of the urogenital and gastrointestinal tract.

The physiological transmission of information for the relaxation (atony) of smooth muscle cells is produced by transmitting substances of the blood (hormones) or the nerves (neurotransmitters). Inside the smooth muscle cells, these neurotransmitters produce an increase of cAMP and cGMP, which brings about relaxation. cAMP and cGMP again are degraded by phosphodiesterases (PDE). Inhibitors of the PDE again reduce the degradation of cAMP and cGMP, which results in an increase of these molecules inside the cells and thus in a relaxation of the smooth muscle cells. This is described, for example, by Torphy, Undem in Thorax 46, 512, 1991.

From this publication and from TIPS 12, 19, 1991 as well as Br. J. Pharmacol. 104, 471, 1991, a differentiation of the PDE in different lower esterases, the specific phosphodiesterases (sPDE), is known. In this case, five different sPDEs are distinguished, which are distributed in a varied manner in the individual organs and organ systems and whose effectiveness varies depending on the distribution in the cells. In the mentioned publications as well as in J. Histochem. Cytochem. 35, 72, 1987, J. Urol. 139, 1988 and J. Pharmacol. Exp. Therap. 247, 630, 1988, the occurrence of the different isoenzymes in various tissues is also discussed, i.a., also the occurrence of sPDE I in the ureter (renal duct).

According to Altwein and Jacobi, Urologie [Urology], Enke Verlag Stuttgart, 1987, renal or renal-duct colics have the nature of a wide-spread disease. The colicky pain develops by an intrarenal increase of pressure by the disturbed urine transport as well as by local spasms, which impede the spontaneous passage of a calculus. It results in an impaction of the calculus, which entails the danger of blockage and the associated serious complications. If no spontaneous passage is achieved in patients with calculi, optionally an invasive course of action must be taken with the help of pharmaceutical agents.

A treatment of these diseases takes place symptomatically at this time by strong-acting analgesics for alleviation of pain. A medicinal treatment of the causes of a colic has so far not been possible, since no substances relaxing the smooth muscles without accompanying undesirable, serious systemic side effects (drop in blood pressure, nausea) are known.

Object of the invention is therefore the preparation of highly effective specific therapeutic agents for the modulation of the motility and peristalsis of the hollow organs of the urogenital and gastrointestinal tract, which do not cause any side effects. Surprisingly, it has now been found that the modulation of the motility and peristalsis of the hollow organs of the urogenital and gastrointestinal tract is influenced by the inhibition of the sPDE IV. A specific inhibition of this isoenzyme has a relaxing effect on the smooth muscles and makes possible the treatment of diseases of the urogenital and gastrointestinal tract, in which the relaxation of the smooth muscles is desired, such as, for example, the treatment of kidney and ureter diseases, the treatment of diseases of the biliary tracts or disturbances of the gastrointestinal tract, such as disturbances such as the irritable colon or stomach cramps. For example, a specific inhibition of this isoenzyme has a relaxing effect on tonicity and peristalsis of the partially or completely occluded renal duct. The passage of the calculus can be fostered and accelerated by the relaxation of the ureter, and a treatment of colic made possible. Because of the relaxing effect on the smooth muscles, inhibitors of sPDE IV can be used in combination with the usual contrast media to improve the diagnosis of the above-mentioned diseases. The administration of the inhibitors of sPDE IV can take place shortly before, after or simultaneously with an administration of x-ray, ultrasonic or NMR contrast media.

Object of the invention is therefore the use of specific inhibitors of sPDE IV for the production of pharmaceutical agents for the modulation of motility and peristalsis of the hollow organs of the urogenital and gastrointestinal tract, pharmaceutical agents containing sPDE IV inhibitors for the mentioned object as well as their use as adjuvants in diagnostic agents.

Preferred inhibitors of the sPDE IV are, for example:
1. 1,3-Dibutyl-3,7-dihydro-7-(2-oxopropyl)-1H-purine-2,6-dione (Denbufyllines, BRL 30892),
2. 4-[(3-butoxy-4-methoxyphenyl)methyl]-2-imidazolidinone (Ro 20-1724),
3. 4-[3-(cyclopentyloxy)-4-methoxyphenyl]-2-pyrrolidinone (rolipram, ZK 62711),
4. 5,6-diethoxybenzo[b]thiophene-2-carboxylic acid (Tibenelast, LY 186655),
5. 3-ethyl-1-(3-nitrophenyl)-2,4(1H,3H)-quinazolinedione (nitraquazones, TVX 2706),
6. 6-(3,6-dihydro-6-methyl-2-oxo-2H-1,3,4-thiadiazin-5-yl)-1-(3,4-dimethoxybenzoyl)-1,2,3,4-tetrahydro-4,4-dimethylquinoline (EMD 54622),
7. 1-ethyl-4-[(1-methylethylidene)hydrazino]-1H-pyrazolo[3,4-b]pyridine-5-carboxylic acid ethyl ester (etazolates),
8. N-hydroxy-5,6-dimethoxy-benzo[b]thiophene-2-carboximidamide (Org 30029),
9. 2-amino-6-methyl-4-propyl-(1,2,4)triazolo[1,5-a]pyrimidin-5(4H)-one (ICI 63197) or
10. 6-[4-(difluoromethoxy)-3-methoxyphenyl]-3(2H)-pyridazinone (zardaverines)

as well as their pharmacologically compatible salts.

The compounds are known as being effective, e.g., in diseases of the respiratory system, for suppression of inflammation or in the case of diseases of the central nervous system.

As preferred sPDE IV inhibitor, racemic or optically active rolipram can be considered, whose production can take place according to U.S. Pat. No. 4,193,626 or according to WO 92/06077.

The administration of the smallest dosages of a specific inhibitor, e.g., of the sPDE IV inhibitor rolipram in a dosage of $10^{-7}$ mol/l (FIG. 4) already relaxes the ureter, without significant effects on other organs, especially on vessels, being able to be observed. This was shown in vitro in human ureter layers.

Studies on living animals (rabbits) led to the same results. Here also, the renal duct was made wider by intravenous administrations of sPDE IV inhibitors such as rolipram, without side effects such as a drop in blood pressure having occurred.

In contrast with this, the administration of unspecific PDE-inhibitor papaverine resulted in pronounced side effects of the circulatory system.

Our test results show that specific phosphodiesterase-IV inhibitors and especially racemic or optically active rolipram can be used for the modulation of the motility and peristalsis of the urogenital and gastrointestinal tract. By the relaxation of the smooth muscles, for example, the passage of calculi is facilitated and colics are prevented. For example, they can be used by the relaxation of the ureter for acceleration and facilitation of the passage of kidney and ureter calculi as well as prevent or end colics.

For the production of the pharmaceutical agents, in addition to the usual adjuvants, vehicles and additives, an effective dose of the inhibitors of sPDE IV or their salts is used in the above-mentioned indications.

The pharmacologically compatible salts are obtained in the usual way by neutralization of the bases with inorganic or organic acids. As inorganic acids, for example, hydrochloric acid, sulfuric acid, phosphoric acid or hydrobromic acid are suitable, as organic acids, for example, carboxylic, sulfo or sulfonic acids, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, malic acid, salicylic acid, 3-aminosalicylic acid, ascorbic acid, embonic acid, nicotinic acid, isonicotinic acid, oxalic acid, amino acids, methanesulfonic acid, ethanesulfonic acid, 2-hydroxyethanesulfonic acid, ethane-1,2-disulfonic acid, benzenesulfonic acid, 4-methylbenzenesulfonic acid or naphthalene-2-sulfonic acid are suitable.

The dosage of the active ingredients can vary depending on the method of administration, age, weight of the patient, type and severity of the disease to be treated and similar factors.

The daily dose can be given as a single dose to be administered once or subdivided into 2 or more daily doses and corresponds in general to the dose that is known as an effective dose of the respective compound.

The daily total dose of rolipram is usually 0.001–10 mg/per person, preferably 0.01–5 mg/per person. If (−) rolipram is administered as active ingredient, the daily dose is preferably 0.001–5 mg. But by several days of titration, the total dose can be increased significantly if necessary.

As form of administration, oral, intravenous, intraluminar preparations are suitable. The latter are above all solutions and preparations, as they are also used for parenteral administration.

Preparations for parenteral administration can be available in separate dosage unit forms, such as, e.g., ampoules or vials. Preferably, solutions of the active ingredient are used, preferably aqueous solutions and above all isotonic solutions, but also suspensions. These forms of injection can be made available as ready-to-use preparations or are prepared only directly before the use by mixing the active compound, for example, the lyophilizate, optionally with additional solid vehicles, with the desired solvent or suspending agent.

The usual galenical preparation forms, such as tablets, coated tablets, capsules, dispersible powders, granular materials, aqueous or oily suspensions, syrups, juices or drops are used orally.

Solid types of pharmaceuticals can contain inert adjuvants and vehicles, such as, e.g., calcium carbonate, calcium phosphate, sodium phosphate, lactose, starch, mannitol, alginates, gelatin, guar gum, magnesium or aluminum stearate, methyl cellulose, talc, highly dispersed silicic acids, silicone oil, higher-molecular fatty acids (such as stearic acid), gelatin, agar-agar or vegetable or animal fats and oils, solid high-molecular polymers (such as polyethylene glycol); for oral administration, suitable preparations can optionally contain additional flavoring substances and/or sweeteners.

Liquid types of pharmaceuticals can be sterilized and/or optionally contain adjuvants, such as preservatives, stabilizers, wetting agents, penetration agents, emulsifiers, spreading agents, solubilizers, salts for adjusting osmotic pressure or for buffering and/or viscosity regulators.

Such additives are, for example, tartrate and citrate buffer, ethanol, complexing agents (such as ethylenediaminetetraacetic acid and their nontoxic salts). To adjust the viscosity, high-molecular polymers are suitable, such as, for example, liquid polyethylene oxide, carboxymethyl celluloses, polyvinylpyrrolidones, dextrans or gelatin. Solid vehicles are, for example, starch, lactose, mannitol, methyl cellulose, talc, highly-dispersed silicic acids, higher-molecular fatty acids (such as stearic acid), gelatin, agar-agar, calcium phosphate, magnesium stearate, animal and vegetable fats, solid high-molecular polymers (such as polyethylene glycol).

Oily suspensions for parenteral or topical (in this case intraureteral) uses can be vegetable, synthetic or semisynthetic oils, such as, for example, liquid fatty acid esters with respectively 8 to 22 C atoms in the fatty acid chains, for example, palmitic, lauric, tridecanoic acid, margaric acid, stearic acid, arachidic acid, myristic acid, behenic acid, pentadecanoic acid, linoleic acid, elaidic acid, brassidic acid, erucic acid or oleic acid, which can be esterified with monovalent to trivalent alcohols with 1 to 6 C atoms, such as, for example, methanol, ethanol, propanol, butanol, pentanol or their isomers, glycol or glycerol. Such fatty acid esters are, for example, commercially available [one or two letters illegible]iglyols, isopropyl myristate, isopropyl palmitate, isopropyl stearate, PEG 6-capric acid, caprylic/capric acid esters of saturated fatty alcohols, polyoxyethylene glycerol trioleates, ethyl oleate, waxy fatty acid esters, such as artificial duck preen fat, coconut fatty acid-isopropyl ester, oleic acid oleyl ester, oleic acid decyl ester, lactic acid ethyl ester, dibutyl phthalate, adipic acid diisopropyl ester, polyol fatty acid ester, i.a. Also suitable are silicone oils of different viscosity or fatty alcohols, such as isotridexyl alcohol, 2-octyldodecanol, cetylstearyl alcohol or oleyl alcohol, fatty acids, such as, for example, oleic acid. Further, vegetable oils such as castor oil, almond oil, olive oil, sesame oil, cottonseed oil, peanut oil or soybean oil can be used. The mentioned substances have, moreover, the properties of a spreading agent, i.e., an especially good spreading takes place on the skin.

As solvents, gel formers and solubilizers, water or water-miscible solvents are suitable. Suitable are, for example, alcohols, such as, for example, ethanol or isopropyl alcohol, benzyl alcohol, 2-octyldodecanol, polyethylene glycols, phthalates, adipates, propylene glycol, glycerol, di- or tripropylene glycol, waxes, methyl cellosolve, cellosolve, ester, morpholines, dioxan, dimethyl sulfoxide, dimethylformamide, tetrahydrofuran, cyclohexanone, etc.

As film formers, cellose ethers can be used that can be dissolved or caused to swell both in water and in organic solvents and after the drying, form a type of film, such as, for example, hydroxypropyl cellulose, methyl cellulose, ethyl cellulose or soluble starches.

Mixed forms between gel formers and film formers are also entirely possible. Here, above all ionic macromolecules are used, such as, e.g., sodium carboxymethyl cellulose, polyacrylic acid, polymethacrylic acid and their salts, sodium amylopectin semiglycolate, alginic acid or propylene glycol alginate as sodium salt, gum arabic, xanthan gum, guar gum, or carrageenan.

As other formulation additives, there can be used: glycerol, paraffin of various viscosity, triethanolamine, collagen, allantoin, novantisolic acid, perfume oils.

Also, the use of surfactants, emulsifiers or wetting agents can be necessary for the formulation, such as, for example, of Na-lauryl sulfate, fatty alcohol ether sulfates, di-Na-N-lauryl-β-iminodipropionate, polyoxyethylated castor oil or sorbitan monooleate, sorbitan monostearate, cetyl alcohol, lecithin, glycerol monostearate, polyoxyethylene stearate, alkylphenolpolyglycol ether, cetyltrimethylammonium chloride or mono-/dialkylpolyglycol ether-orthophosphoric acid-monoethanolamine salts.

Stabilizers, such as montmorillonites or colloidal silicic acids for stabilizing emulsions or for preventing the degradation of the active substances, such as antioxidants, for example, tocopherols or butyl hydroxyanisole, or preservatives, such as p-hydroxybenzoic acid ester, can also be optionally necessary for preparing the desired formulations.

To promote the penetration, intraureteral formulations preferably contain organic, readily compatible solvents, such as ethanol, methyl pyrrolidone, polyethylene glycol, oleyl alcohol, octanol, linoleic acid, triacetin, propylene glycol, glycerol, solketal or dimethyl sulfoxide.

The production, filling and the sealing of the preparations takes place under the usual antimicrobial and aseptic conditions. Also, for topical or transdermal use, a packaging takes place as much as possible in separate dosage units to facilitate the handling, here as well as in parenteral forms optionally for reasons of stability by separate packaging of the active ingredients and respectively their combinations as lyophilizate, optionally with solid vehicles, and the necessary solvents, etc.

EXAMPLE 1

Injection Solution 50 mg of rolipram is dissolved with 750 mg of NaCl in distilled water, adjusted to pH 3.7 with 1 N HCl and filled up to 100 ml with distilled water and packaged in 0.5 ml ampoules.

EXAMPLE 2

Solution for Topical Application

A solution for topical application is prepared from 500 mg of rolipram, 2 ml of isopropyl myristate and 10 ml of ethanol and packaged in dosage units of 2 ml each.

The effectiveness of the pharmaceutical agents for the teaching according to the invention is substantiated by the following pharmacological studies:

Fresh human ureter removed in the operation is cut into small strips (about 3×10 mm). These are then installed in a bath with a nutrient solution, which assures the survival of the organ strips. By a coupling of the organ strips to a sensor, changes of length of the organ strip can be recorded and thus effects of medicines, which are provided in the organ bath-nutrient solution, are studied based on the change of length (increase or decrease) of the organ strip. At the beginning of the test, the organ strips are contracted with a standard medicine, e.g., noradrenaline, suitable for this purpose. After the occurrence of contractions of the organ strips, an inhibitor of a specific phosphodiesterase is now provided in the organ bath solution in increasing dosage ($10^{-7}$, $10^{-6}$, $10^{-5}$, etc., mol/l) and the thus triggered relaxation is measured. The results obtained can be assigned essentially to the entire organism, since human tissue was used, and the metabolic processes examined occur more quickly in the total organism and therefore the medicines also act more quickly.

In FIG. 1 to FIG. 5, the results of these organ bath tests are represented.

Figure 1:
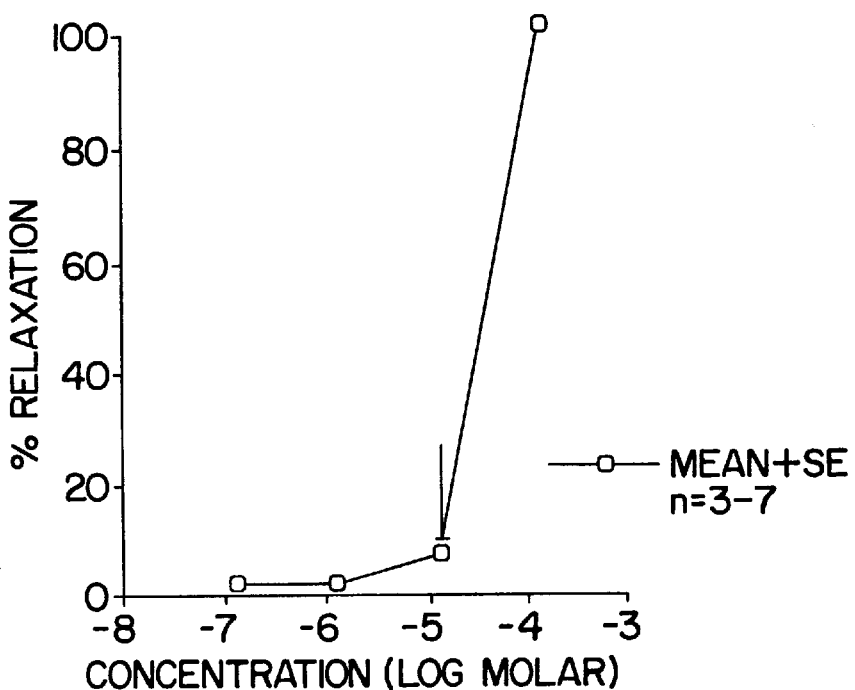
FIG. 1 shows the relaxing effect of cumulatively increasing concentrations of papaverine, a nonspecific phosphodiesterase inhibitor, on human ureter strips precontracted with 80 mmol of KCl. The curve shows the average values of measurements of 3 to 7 ureter strips each.
Figure 2:
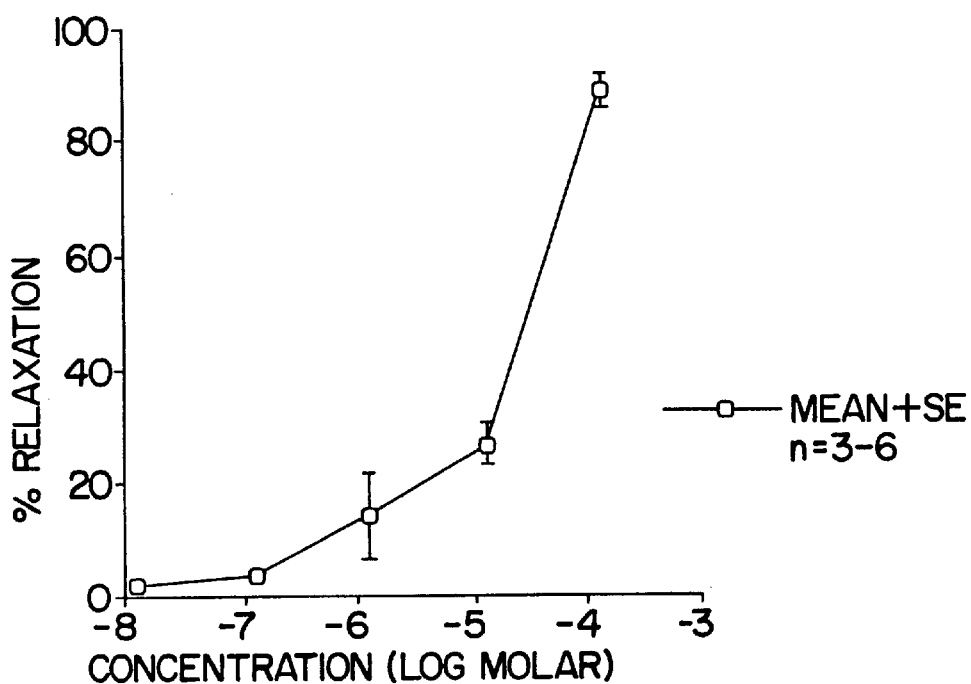
FIG. 2 shows the relaxing effect of cumulatively increasing concentrations of quazinone, an inhibitor of sPDE III on human ureter strips precontracted with 80 mmol of KCl. The curve shows the average values of measurements of 3 to 6 ureter strips each.
Figure 3:
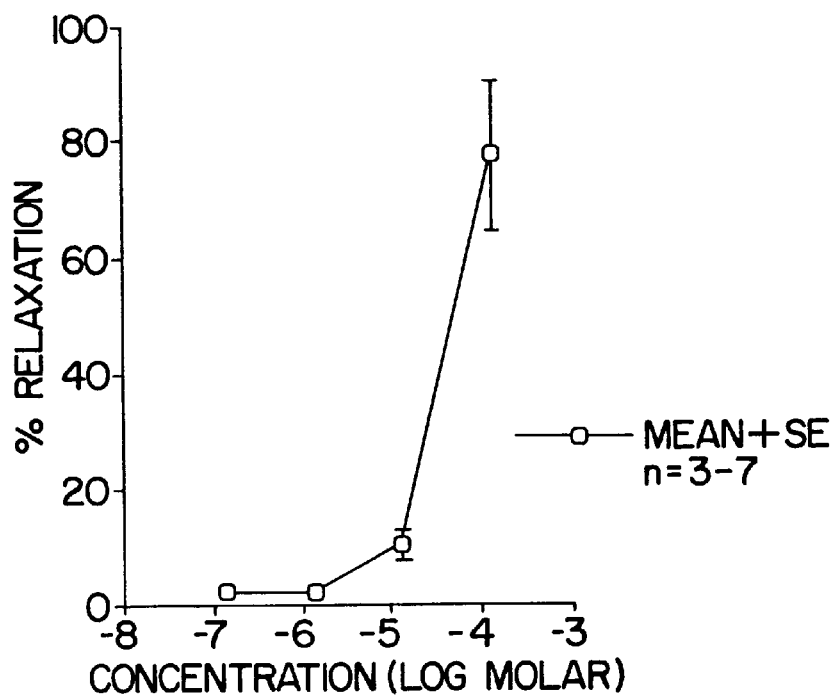
FIG. 3 shows the relaxing effect of cumulatively increasing concentrations of zaprinast, an inhibitor of sPDE V on human ureter strips precontracted with 80 mmol of KCl. The curve shows the average values of measurements of 3 to 6 ureter strips each.
Figure 4:
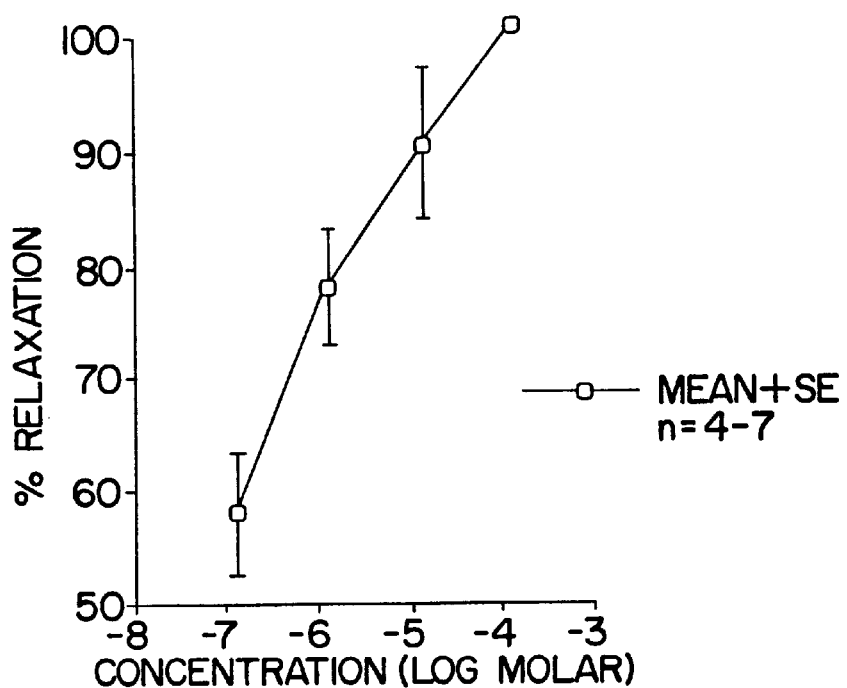
FIG. 4 shows the relaxing effect of cumulatively increasing concentrations of rolipram, an inhibitor of sPDE IV on human ureter strips precontracted with 80 mmol of KCl. The curve shows the average values of measurements of 4 to 7 ureter strips each.
Figure 5:
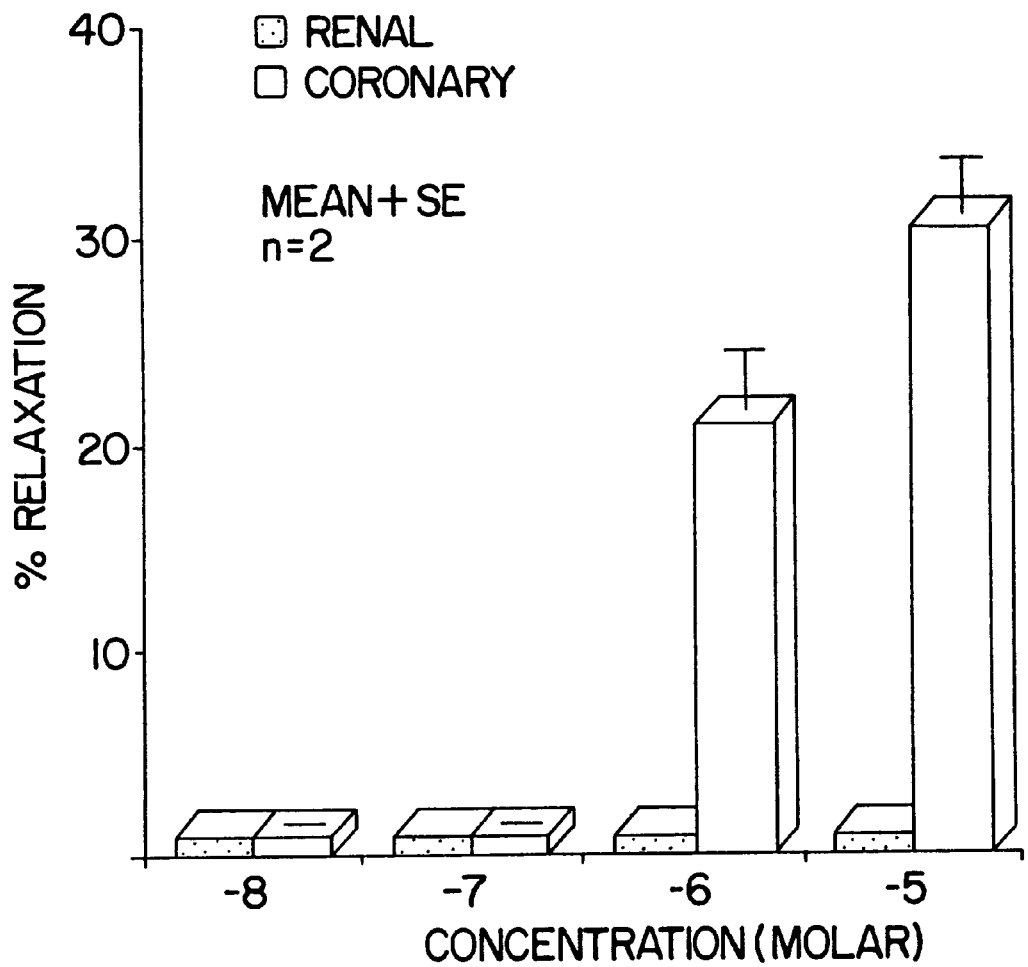
FIG. 5 shows a comparison of the relaxing effect of rolipram on renal and coronary arterial strips.

The tests concerning FIG. 5 were performed analogously to the studies of ureter strips and substantiate in a more precise way the specific relaxing effect on the ureter tissue, while the renal vascular system is not influenced at all.

The proof whether a compound is suitable for the purpose according to the invention, i.e., is an inhibitor of the sPDE IV, takes place according to known methods, such as, e.g., described by Galwan et al., Arch. Pharmacol. 1990, 342, 221–227 or Nicholson, Br. J. Pharmacol., 1989, 79, 889–897, for example according to the following general methods:

Fresh tissue obtained during an operation is homogenized and then ultracentrifuged. Then, the supernatant is pipetted off and chromatographed. Of the 100 fractions of 70 to 1000 mmol (millimolar), 5 batches each of 30 μl of the enzyme preparation are then produced; each enzyme preparation of a fraction is mixed with a) radioactively-labeled cAMP, b) radioactively-labeled cGMP, c) radioactively-labeled cAMP plus calcium plus calmodulin, d) radioactively-labeled cGMP plus calcium plus calmodulin, or e) radioactively-labeled cAMP plus cGMP plus calcium plus calmodulin. After incubation and completion of the reaction as well as renewed centrifuging, the radioactivity of the samples is measured. The determination of the radioactivity allows the calculation of the enzyme activity in pmol/ml×min. The application of the activity curve allows the identification of fractions, in which the phosphodiesterase activity is especially high. The phosphodiesterase activity of each peak shows a different composition relative to the activity of the 5 different batches. This special composition of the phosphodiesterase activity permits an assignment to a specific phosphodiesterase (sPDE). An inhibitor of an sPDE is now that substance whose concentration, which is necessary to prevent 50% of the substrate hydrolysis ($IC_{50}$) in the peak fraction in question, which contains the specific phosphodiesterase, is smaller by at least 20 times than in other peak fractions. For this purpose, enzyme preparations are again produced as described above. But before the incubation of the enzyme batches, according to a) to e) of the peak fractions, the compound to be tested is now added. According to the above-indicated definition, the renewed determination and application of the enzyme activity then allows the identification of a substance as inhibitor of the specific phosphodiesterase.

What is claimed is:

1. A method of imaging the urogenital or gastrointestinal tract of a host comprising administering an effective amount of a phosphodiesterase type IV inhibitor or a salt thereof; and administering an X-ray contrast media; and imaging said urogenital or gastrointestinal tract using X-ray imaging.

2. A method of claim 1, wherein said phosphodiesterase type IV inhibitor is administered before said contrast media.

3. A method of claim 1, wherein said phosphodiesterase type IV inhibitor is administered at the same time as said contrast media.

4. A method of claim 1, wherein said phosphodiesterase type IV inhibitor is administered after said contrast media.

5. A method of claim 1, wherein said phosphodiesterase type IV inhibitor is administered during said imaging.

6. A method of claim 1, wherein said phosphdiesterase type IV inhibitor is 1,3-Dibutyl-3,7-dihydro-7-(2-oxopropyl)-1H-purine-2,6-dione,
4-[(3-butoxy-4-methoxyphenyl)methyl]-2-imidazolidinone,
4-[3-(cyclopentyloxy)-4-methoxyphenyl]-2-pyrrolidinone,
5,6-diethoxybenzo[b]thiophene-2-carboxylic acid,
3-ethyl-1-(3-nitrophenyl)-2,4(1H,3H)-quinazolinedione,
6-(3,6-dihydro-6-methyl-2-oxo-2H-1,3,4-thiadiazin-5-yl)-1-(3,4-dimethoxybenzoyl)-1,2,3,4-tetrahydro-4,4-dimethylquinoline,
1-ethyl-4-[(1-methylethylidene)hydrazino]-1H-pyrazolo[3,4-b]pyridine-5-carboxylic acid ethyl ester,
N-hydroxy-5,6-dimethoxy-benzo[b]thiophene-2-carboximidamide,
2-amino-6-methyl-4-propyl-(1,2,4)triazolo[1,5-a]pyrimidin-5(4H)-one or
6-[4-(difluoromethoxy)-3-methoxyphenyl]-3(2H)-pyridazinone.

7. A method of claim 1, wherein said phosphdiesterase type IV inhibitor is rolipram.

8. A method of claim 1, wherein said phosphdiesterase type IV inhibitor is (−) rolipram.

9. A pharmaceutical composition comprising:
a phosphodiesterase type IV inhibitor; and
a contrast media for X-ray imaging.

10. A composition of claim 9, wherein the phosphodiesterase type IV is 1,3-Dibutyl-3,7-dihydro-7-(2-oxopropyl)-1H-purine-2,6-dione,
4-[(3-butoxy-4-methoxyphenyl)methyl]-2-imidazolidinone,
4-[3-(cyclopentyloxy)-4-methoxyphenyl]-2-pyrrolidinone,
5,6-diethoxybenzo[b]thiophene-2-carboxylic acid,
3-ethyl-1-(3-nitrophenyl)-2,4(1H,3H)-quinazolinedione,
6-(3,6-dihydro-6-methyl-2-oxo-2H-1,3,4-thiadiazin-5-yl)-1-(3,4-dimethoxybenzoyl)-1,2,3,4-tetrahydro-4,4-dimethylquinoline,
1-ethyl-4-[(1-methylethylidene)hydrazino]-1H-pyrazolo[3,4-b]pyridine-5-carboxylic acid ethyl ester,
N-hydroxy-5,6-dimethoxy-benzo[b]thiophene-2-carboximidamide,
2-amino-6-methyl-4-propyl-(1,2,4)triazolo[1,5-a]pyrimidin-5(4H)-one or
6-[4-(difluoromethoxy)-3-methoxyphenyl]-3(2H)-pyridazinone.

11. A composition of claim 9, wherein the phosphodiesterase type IV is rolipram.

12. A composition of claim 9, wherein the phosphodiesterase type IV is (−) rolipram.

* * * * *